(12) United States Patent
Wright

(10) Patent No.: US 11,167,089 B2
(45) Date of Patent: Nov. 9, 2021

(54) REDUCED SPUTTERING SYRINGE

(71) Applicant: PROVENSIS LIMITED, London (GB)

(72) Inventor: David Dakin Iorwerth Wright, London (GB)

(73) Assignee: Provensis Limited, London (GB)

( * ) Notice: Subject to any disclaimer, the term of this patent is extended or adjusted under 35 U.S.C. 154(b) by 0 days.

(21) Appl. No.: 15/636,004

(22) Filed: Jun. 28, 2017

(65) Prior Publication Data

US 2017/0368262 A1 Dec. 28, 2017

(30) Foreign Application Priority Data

Jun. 28, 2016 (GB) ..................................... 1611185

(51) Int. Cl.
| | |
|---|---|
| *A61M 5/31* | (2006.01) |
| *A61M 5/178* | (2006.01) |
| *A61M 5/48* | (2006.01) |
| *A61B 17/22* | (2006.01) |
| *A61M 5/315* | (2006.01) |

(52) U.S. Cl.
CPC ............ *A61M 5/3129* (2013.01); *A61B 17/22* (2013.01); *A61M 5/178* (2013.01); *A61M 5/3135* (2013.01); *A61M 5/31505* (2013.01); *A61M 5/484* (2013.01); *A61B 2017/22082* (2013.01); *A61M 2005/3131* (2013.01); *A61M 2202/06* (2013.01)

(58) Field of Classification Search
CPC ............ A61M 5/31505; A61M 5/3134; A61M 5/3129; A61M 5/31513; A61M 5/31511; A61M 5/315101; A61M 2005/3131; A61M 2005/31523; A61M 5/14526; A61M 2005/31521; A61M 2202/06; A61M 5/178; A61M 5/3135; A61M 5/484; A61B 17/12181; A61B 17/22; A61B 2017/22082
See application file for complete search history.

(56) References Cited

U.S. PATENT DOCUMENTS

| | | | |
|---|---|---|---|
| 4,354,507 A | 10/1982 | Raitto | |
| 6,050,974 A * | 4/2000 | Allard | A61M 5/3234 |
| | | | 604/110 |

(Continued)

FOREIGN PATENT DOCUMENTS

| | | |
|---|---|---|
| DE | 201 09 678 | 10/2001 |
| FR | 342.630 | 9/1904 |

(Continued)

OTHER PUBLICATIONS

British Search Report issued in Appln. No. GB 1611185.8 dated Dec. 22, 2016.

(Continued)

*Primary Examiner* — Brandy S Lee

(74) *Attorney, Agent, or Firm* — Seager, Tufte & Wickhem, LLP

(57) ABSTRACT

Syringe for dispensing medical foam having a substantially cylindrical barrel with a nozzle at its forward end and a plunger with a substantially cylindrical shaft disposed within the barrel. A flexible annular flange is provided on the inner surface of the barrel which extends toward the nozzle to contact the shaft and form a seal between the barrel and the plunger.

9 Claims, 2 Drawing Sheets

(56) References Cited

U.S. PATENT DOCUMENTS

| | | | |
|---|---|---|---|
| 6,695,317 B2 * | 2/2004 | Lehnert | B01L 3/0217 |
| | | | 277/436 |
| 8,202,495 B1 * | 6/2012 | Smith | B01L 3/0275 |
| | | | 422/500 |
| 8,777,906 B1 * | 7/2014 | Gray | A61M 5/3135 |
| | | | 604/189 |
| 2002/0185821 A1 | 12/2002 | Lehnert et al. | |
| 2003/0065291 A1 | 4/2003 | Corrigan, Jr. | |
| 2014/0288507 A1 * | 9/2014 | Samuel | A61M 5/31513 |
| | | | 604/222 |
| 2015/0086448 A1 | 3/2015 | Uldry | |
| 2016/0129197 A1 * | 5/2016 | Hetting | A61M 5/3202 |
| | | | 604/194 |

FOREIGN PATENT DOCUMENTS

| | | |
|---|---|---|
| FR | 1.224.977 | 6/1960 |
| WO | WO 00/72821 A1 | 12/2000 |
| WO | WO 2005/023678 A1 | 3/2005 |

OTHER PUBLICATIONS

Extended European Search Report issued in Appln. No. EP 17178414.3 dated Nov. 22, 2017.

* cited by examiner

REDUCED SPUTTERING SYRINGE

This application claims priority to British Patent Application No. GB 1611185.8 filed Jun. 28, 2016, the entire contents of which are hereby incorporated by reference.

The present invention relates to a reduced sputtering syringe, that is, a medical syringe which enables intravenous injection of medical foams without uncontrolled, explosive release of the syringe contents. In particular, the syringe is designed with component parts which cooperate with low friction such that it is suitable for dispensing and administering injectable foams i.e. for receiving foam from a pressurized or other source of foam and for subsequently administering the foam intravenously to a patient. The invention is particularly suitable for dispensing medical microfoams, such as sterile, clinical grade sclerosing foam for the treatment of varicose veins and other venous conditions.

BACKGROUND OF THE INVENTION

Intravenous administration of sclerosing foam is widely used in the treatment of varicose veins. In the treatment of smaller varicosities (such as spider and reticular veins), where multiple, small volumes of foam are often injected, it is important that the physician has control over the rate of delivery of the sclerosing foam in addition to the volume delivered.

Medical syringes typically comprise a cylindrical barrel within which is disposed a plunger to form a chamber for receipt of a composition to be administered to a patient. Typically, the plunger head forms an interference fit within the barrel to form a fluid-tight seal and prevent leakage from the syringe. The plunger heads acts as a piston, and forces the syringe contents from the chamber when the plunger is depressed. As is well known, syringes are calibrated with volume markings to ensure administration of a known dose to the patient. However, the user must apply significant force to overcome the friction created by the interference fit between the plunger and barrel. This reduces control over administration from the syringe, and can make it difficult for a physician to deliver small volumes accurately. The forces applied by the user to overcome friction to initiate plunger movement (i.e. breakout force) and maintain plunger movement (i.e. glide force) causes compression and, consequently, pressurization of the syringe contents. Injection of fluids under pressure can cause sputtering (i.e. uncontrolled or explosive release; ejaculation) of the syringe contents, which makes controlled administration difficult. This is particularly apparent when injecting small volumes, typically in the range of from about 0.5 ml to about 10 ml. Sputtering of syringe contents can have consequences for the patient, ranging from discomfort during injection to mechanical disruption of vessel walls that can lead to extravasation of syringe contents and damage to surrounding tissues. The problem of sputtering is more pronounced for administration of foam than liquid because foam, having a large gas content, is significantly more compressible than liquid, even within the small volume of a syringe. The treatment of varicose veins is often accomplished under ultrasound guidance so that the physician can observe, in real time, foam filling the vein, displacing blood and inducing venospasm. Better clinical outcomes are observed if the entire segment is filled with foam, and treatment is typically concluded when the physician observes complete filling of the vein, rather than by administering a predetermined volume of foam. Slow, smooth controlled injection of foam is therefore more important to the physician than knowing precisely what volume of foam has been injected.

Traditionally, the problem of sputtering is avoided by reducing friction within the syringe by applying coatings on the inner surface of the syringe barrel. The coatings are designed to lubricate the inner wall of the syringe barrel to provide reduced friction and smoother gliding at the point of contact between the plunger and the barrel. However, such coatings tend to be silicone-based lubricants, which are not suitable for the injection of injectable foams because such lubricants have surfactant properties which are known to accelerate degradation of sclerosing foams. Syringes coated with silicone and other lubricants are, consequently, not suitable for use in foam sclerotherapy.

U.S. Pat. No. 4,354,507 describes a syringe having a plunger with a compressible elastomeric tip provided with a peripheral annular wiper lip that makes contact with the inner surface of the syringe barrel. This interference fit arrangement provides an effective seal that is improved as force is applied to the plunger. This syringe is intended for taking blood, not for intravenous injection. The wiper lip is angled and constructed so as to provide reduced resistance as the syringe plunger is withdrawn but, as the reduced resistance comes from the wiper lip being angled in the direction of the withdrawing plunger, it will be understood that this angular orientation causes increased resistance when the plunger is subsequently depressed to expel the contents. This syringe doesn't address or overcome the problem of syringe sputtering when administering foam to a patient intravenously. In fact, the syringe described is wholly unsuitable for administration of foam because increased pressure will be necessary to overcome the increased friction created when the syringe plunger is depressed. This will increase the frequency and severity of sputtering.

SUMMARY OF THE INVENTION

Accordingly, there remains a need for a syringe in which sputtering is reduced, or even eliminated, when the plunger is depressed such that foam can be delivered to a patient in a smooth and controlled manner, improving not only handling and administration of the foam but also improving therapeutic efficacy and patient comfort.

The present invention enables improved foam administration to patients by providing a low friction syringe, which results in a lowering of breakout and glide forces during injection, which, in turn, reduces or even eliminates sputtering i.e. the uncontrolled or explosive expulsion of the syringe contents.

Accordingly, in a first aspect the present invention provides a syringe for dispensing medical foam comprising:

a substantially cylindrical barrel comprising a nozzle at its forward end; and a plunger comprising a substantially cylindrical shaft disposed within the barrel, characterised in that:

a flexible, annular flange is provided on the inner surface of the barrel and extend toward the nozzle to contact the shaft and form a seal between the barrel and the plunger.

The seal is not formed by a traditional interference fit such as that usually formed by direct contact between an enlarged plunger head/piston and the inner wall of the syringe barrel in a traditional syringe. Rather, the seal is formed by a flexible, annular flange, which is seated on the inner surface of the syringe barrel. The annual flange comprises a base or seat surface, which rests against or is affixed to the inner surface of the syringe barrel and an inwardly extending portion that extends radially inwardly to an end forming a sealing edge against the outer wall of the syringe plunger. The inwardly extending portion and the end are free of direct attachment to the inner surface of the syringe barrel. The shape and orientation of the flange and the angle of contact between the flange and the shaft is arranged to ensure that depression of the plunger requires application of lower breakout force and lower glide force when compared with traditional syringes. As a result, the barrel does not require additional components to relieve or reduce friction, such as coatings or lubricants. The shape and orientation of the flange alone reduces the amount of force required to administer syringe contents through the nozzle and sputtering of the syringe contents is avoided or reduced as a consequence.

The syringe is very simple and cheap to manufacture because standard components, e.g. syringe barrels of standard size, volume and shape can be used, ideally without coatings or lubricants having been pre-applied. As such, the syringe has a typical longitudinally coaxial barrel and plunger arrangement and is operated in the same manner. It is suitable for receiving or withdrawing foam from any source, to which it can be attached in a similar manner to a traditional syringe, for example, by means of a Luer lock or similar attachment. It can be filled from a foam generating device or by simple aspiration (i.e. withdrawal of the plunger). In particular, the syringe can be used to receive foam from a pressurized canister, for example as described in WO 2005/023678 and in WO 00/02821. In this arrangement, foam is dispensed directly into the syringe through the nozzle. The plunger is forced back into a withdrawn position as the syringe is filled to a desired volume, and the syringe is then disconnected from the foam generating device. A suitable delivery conduit, for example, a hypodermic needle or catheter, is then attached so that foam can be administered from the syringe to a patient.

The syringe barrel is a traditional syringe barrel, comprising a substantially cylindrical bore and being closed at a forward end save for a nozzle and open at a rearward end to receive a plunger. The barrel walls have an inner surface that faces inward (i.e. into the substantially cylindrical bore) and an outer surface. The inner surface typically lacks a friction reducing coating, e.g. lubrication but coatings are contemplated within the scope of the invention provided they do not disrupt the foam or accelerate foam degradation. Substantially cylindrical means that the bore has a circular cross-section that is substantially constant along its length. The barrel is made of a rigid plastic that is biocompatible such that it is safe to use for administration of pharmaceutical compositions to a patient. Suitable plastics include, for example, polypropylene, polyethylene, cyclopolyolefin, polycarbonate, polymethyl-methacrylate, polystyrene, polyvinyl chloride and acrylonitrile-butadiene-styrene copolymer (ABS).

The nozzle is a traditional syringe nozzle. Typically the nozzle comprises a structure suitable for engaging a foam dispensing device, for example a pressurized canister, and also for engaging a hypodermic needle or a catheter for administration of syringe contents to a patient. Preferably the nozzle comprises a Luer attachment that permits use of the syringe with standard hypodermic needles and catheters.

As described above, a fluid-tight seal is provided by an annular flange, which extends from the inner surface of the barrel to contact the plunger shaft. In a preferred embodiment, the flange is not planar but has a frustoconical shape which extends from its seat, out of plane, towards the plunger, in the direction of the syringe nozzle In other words, considering the nozzle as being the front end of the syringe, the flange extends generally forwards and generally inwards toward the plunger shaft. As a result, the flange contacts the shaft at an acute angle (i.e less than 90 degrees) with respect the plunger shaft. Put another way, the angle between the outer surface of the front end of the plunger shaft is greater than 90 degrees. The flange extends radially inwardly and axially forwardly from its seat/base on the inner surface of the barrel to contact the shaft and form a seal between the barrel and the plunger at a point which is forward of the base The annular flange contacts the syringe plunger and forms a seal which is ring-shaped around the entire circumference of the inner surface of the barrel. The flange is typically in the form of an out-of-plane (or frusto-conical) gasket, which is formed as a single continuous piece of flexible material, to avoid stress-fractures and to aid assembly into the syringe.

The flange is flexible. In other words, it is capable of bending, stretching, being compressed or being otherwise deformed without breaking. The flange may be elastic, i.e. it may be able to resume its normal shape spontaneously after being stretched or compressed. The flange is made of a flexible polymer that is impermeable to the contents being administered from the syringe. Typically, the flange is stretchable at pressures encountered when dispensing foam or administering foam to a patient. Such pressures can be between 0 and 4 bar above ambient pressure, but more typically they are between 0 and 1 bar above ambient pressure. Stretching of the flange prevents compression of syringe contents as force is applied to the plunger, and this prevents unwanted sputtering. Utilizing flanges with a degree of elasticity enable embodiments of the device in which the flange extends from the barrel wall and either does not contact the plunger and/or form a seal unless stretched. Such stretching occurs under the influence of foam preset in the syringe, which exerts a force against the flange to press it against the barrel and form a seal. Such embodiments are advantageous because friction is only created when the filled; and the orientation and shape of the flange means that only reduced friction need be overcome when injecting foam from the syringe. Suitable polymers for forming the flange include nylon and polyvinyl amide, and other polymers that may be used include polypropylene, polyethylene, polybutylene resin, thermoplastic elastomer and ethylene-vinyl acetate copolymer (EVA).

The flange is seated against the inner surface of the syringe barrel and the seat may take the form of a permanent attachment to the inner surface of the barrel. Attachment can be by any means that fixes the location of the flange within the barrel, such as glue, welding or molding of the flange and barrel in a single form. This will fix the position of the seat within the syringe barrel, and avoids movement of the flange and associated loss of seal. Preferably and conveniently, the flange is attached to the inner surface of the barrel by glue. This simplifies syringe manufacture by allowing suitable flanges to be manufactured and affixed to standard syringe barrels Alternatively, the flange can be resiliently retained in a desired position within the barrel. In such an arrangement the flange is made of resilient material. It should have a diameter equal to or larger than that of the syringe barrel bore to ensure that sufficient force is applied to the inner surface of the barrel to keep it in place. It is retained against the inner surface of the barrel by resilient forces exerted radially outwardly against the barrel. This simplifies manufacture of the syringe as adhesive application or welding steps are not required.

The annular flange can be attached to the inner surface of the barrel at any point along its length, i.e. at any point between the forward closed end and the rearward open end of the barrel provided a sufficient volume is created for the collection and administration of foam. Typically, the flange is attached close to the rearward, open end of the barrel. This permits for increased volume of foam to be aspirated or received into the syringe for administration to a patient. However, it may be desirable to attach the flange closer to the forward, closed end of the barrel where the syringe is to be used for administration of smaller volumes. Forward attachment of the flange is particularly advantageous as it allows space for inclusion of guide means within the syringe as discussed below.

As outlined above, the flange is flexible. Typically the flange will be flexible over its entire surface area but equally it may flex over a portion of its surface area. For example, the flange may flex in the region that contacts the shaft of the plunger and/or the region adjacent to that which contacts the plunger but be more rigid in the region of the base or seat where the flange is positioned against the inner surface of the barrel. Provision of flexible regions within the flange allows for improved integrity of the seal with reduced flange flexing as the plunger is withdrawn from or depressed into the barrel.

The flange is preferably tapered from a thicker base/seat to have reduced thickness at the point where it contacts the plunger shaft. A region of reduced thickness provides a reduced contact area between the flange and plunger or provides a contact area which has increased flexibility, and this reduces the breakout and glide forces that resist movement of the plunger past the flange while maintaining a seal.

The flange generally extends from a thicker base portion seated on the inner surface of the barrel to a thinner portion which contacts the plunger at an angle as detailed above. The flange typically has a frustoconcial shape which, in cross section, has generally triangular shaped walls. Alternatively, however, the flange is generally frustoconical but with concave side walls i.e. walls which are shaped to curve between the base and the contact point. The curve may extend over a portion of the flange or over the entire flange. A curved flange advantageously biases the flange for contact with the shaft and for effective seal formation between the plunger and the barrel. Additionally, where the flange is formed with concave profile, it can be tailored to provide a larger surface area facing the syringe contents which leads to further reduced pressure on the flange and reduced syringe breakout and glide forces.

Alternatively, the flange walls may comprise a kink. In other words, it may include any combination of straight and/or curved portions that lie at acute, obtuse or right angles to each other. Such kinks can provide dimpling, folding, puckering or bellowing of the flange. While providing an enlarged surface area facing the syringe contents, a kinked flange provides for flange deformation and flexing at specified positions to improve pressure distribution and consequent breakout and glide forces.

Irrespective of the precise shape of the flange walls, the flange generally extends to an annular edge having a circumference that is equal to or less than the outer circumference of the shaft. The annular edge contacts the lateral surface of the shaft to form the seal between the plunger and the barrel. The circumference of the annular edge ensures that a fluid-tight seal is maintained when the plunger is moved within the barrel.

In a particular embodiment, the flange extends to an annular edge having a circumference greater than the outer circumference of the shaft such that it either does not contact the plunger or contacts the plunger but fails to form a seal until foam is contained in the barrel, at which point, foam presses against the flange and deforms the flange such that it contacts the shaft to form a seal between the barrel and the plunger. In this embodiment, it will be understood that a small volume of foam may be wasted as the syringe is filled but this embodiment is particularly advantageous because there is little or no friction to overcome as the syringe is filled with foam (because the flange does not provide sealing contact with the plunger) but when the syringe is filled with foam and is ready to be injected into a patient, the flange creates a seal but, as described above, the shape and orientation of the flange means that reduced breakout and glide forces need be overcome when the foam is injected. This has the practical advantage of allowing the physician to inject the foam slowly and smoothly, which is likely to be more important during treatment than precise or metered dosing of foam.

The plunger has a substantially cylindrical shaft disposed within the barrel. The lateral, outer, surface of the shaft faces the inner surface of the barrel walls, and the forward portion of the shaft is located between the seal formed with the flange and the forward end of the barrel. Substantially cylindrical means the shaft has a circular cross-section that is of substantially constant diameter. The circular cross-section enables good contact by the annular edge of the flange along the lateral surface of the shaft to form a seal between the barrel and the plunger. The substantially cylindrical shaft has a circular cross-section along at least that portion of its length which is contacted by the flange to form a seal between the barrel and the plunger. The shaft may have a circular cross-section along its entire length or along a portion of its length. A circular cross-section along the entire length of the shaft is advantageous as it maintains the torsional rigidity of the plunger. A circular cross-section along only a portion of the shaft maintains the advantageous shape while permitting reduction of the amount of material used to manufacture the plunger. Optionally, the shaft can comprise a hollow portion or it can be hollow. The cross-sectional properties of the shaft can vary as described above, but a shaft comprising a hollow portion or being bellow is advantageous as it requires less material to make and thereby reduces cost of manufacture. Additionally, this reduces the weight of the syringe and eases its use by a physician while maintaining the torsional rigidity of the plunger in use. In a preferred embodiment the hollow portion of the shaft includes a waste chamber, which waste chamber comprising an aperture in contact with the syringe chamber so that fluid can flow, or overflow, from the syringe chamber to the waste chamber. This removes the need for a purging step to void the syringe bore of air or other waste when filling it with foam.

In particular embodiments, the syringe as described above further comprises a guide means to align the syringe plunger within the syringe barrel. This is particularly useful in circumstances where the shape and orientation of the flange means there is little or no contact between the syringe barrel and plunger. The guide means typically aligns the plunger longitudinally. Longitudinal alignment advantageously restrains the longitudinal axes of the plunger and barrel as the plunger is moved within the barrel. The guide means may also align the plunger by preventing it from rotating within the barrel. The guide means may align the plunger longitudinally and by preventing it from rotating within the barrel. The guide means can comprise one or more projections from the inner surface of the barrel or from the plunger or from both the inner surface of the barrel and from the plunger. The one or more projections are arranged to maintain a uniform gap between the plunger and the barrel at the point where the flange contacts the shaft. This prevents the seal between the barrel and the plunger from being broken as the plunger is moved. Optionally, the guide means is arranged on the inner surface of the barrel to align the plunger with the barrel. This is advantageous because the guide does not move with respect to the flange and therefore it cannot restrict plunger movement past the flange or interfere with the seal between the plunger and the barrel.

In a particular embodiment, the guide means comprises a non-sealing spacer disposed between the plunger and the barrel and situated rearward of the annular flange, so as to avoid interference with the sealing mechanism The non-sealing spacer may provide slight resistance to movement of the plunger within the barrel such that it provides a sensory feedback to the user that confirms the application of pressure to the plunger. This reduces the possibility that a user will accidentally apply too much pressure and deliver too much foam when using the syringe, but it does not increase the pressure required to depress the plunger sufficiently to cause sputtering of the syringe contents. This improves the safety of foam delivery and improves the user experience from the perspective of the patient and the physician. In a preferred embodiment the non-sealing spacer is an O-ring. This is advantageous as it is a simple and low cost form of non-sealing spacer that is also capable of acting as a guide means.

The syringe may also comprise a stop guard that stops removal of the plunger from the barrel. This prevents the plunger from being withdrawn past the flange and out of the barrel such that the syringe contents are exposed to the atmosphere. Preferably the stop guard comprises a projection from a surface of the plunger shaft and/or from the inner surface of the barrel. Where the stop guard comprises a projection from the surface of the plunger shaft, that projection is arranged such that it cannot pass the flange or a guide means or a complementary projection arranged on the inner surface of the barrel. Where the stop guard comprises a projection from the inner surface of the barrel the projection is arranged such that it prevents the plunger from passing and being withdrawn. This reduces the risk of human error when receiving foam into the syringe from a pressurized canister that might otherwise force the plunger out of the barrel.

BRIEF DESCRIPTION OF THE DRAWINGS

Further features and advantages of the invention will be apparent from the following description of specific embodiments, which is made with reference to the accompanying drawings.

DETAILED DESCRIPTION OF THE INVENTION

Figure 1:
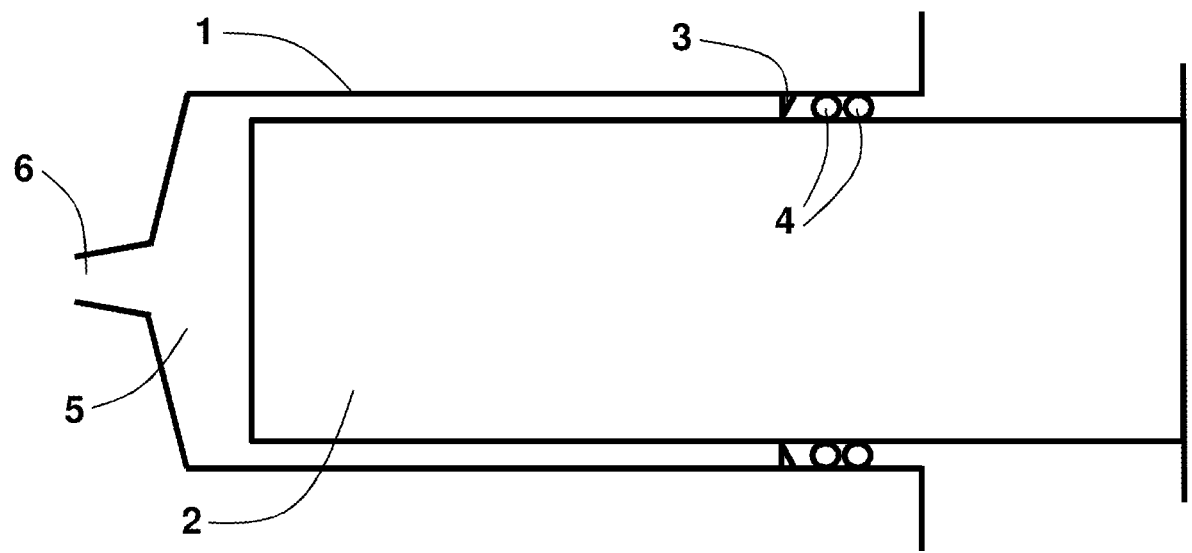
FIG. 1 shows a schematic view of an embodiment of the invention.

A syringe of the invention is shown in FIG. 1 having a barrel 1 with a plunger 2 disposed coaxially within it. A flange 3 is provided around the inner surface of the barrel 1 and makes continuous contact with the lateral surface of the plunger 2 around its entire circumference to form an annular seal such that together, the barrel 1, the plunger 2 and the flange 3 contain the syringe contents 5 within the syringe. Movement of the plunger 2 to a more withdrawn position within the barrel 1 reduces the pressure on the syringe contents 5 and leads to aspiration of foam into the syringe through the syringe nozzle 6. Conversely, depression of the plunger 2 within the barrel 1 leads to increased pressure on the syringe contents 5 and expression of foam from the syringe through the nozzle 6.

The flange 3 is tapered from abase and has a decreasing thickness along its length, having its narrowest profile at the point in contact with the plunger 2. This tapering provides a reliable seal between the flange 3 and the plunger 2 while generating reduced breakout and glide forces to resist the plunger 2 being moved within the barrel 1.

The syringe also includes an optional guide means comprising a non-sealing spacer consisting of two O-rings 4 that serve to position the plunger 2 centrally within the barrel 1 and ensure that the flange 3 remains in continuous contact with the plunger 2 about its entire circumference.

Figure 2:
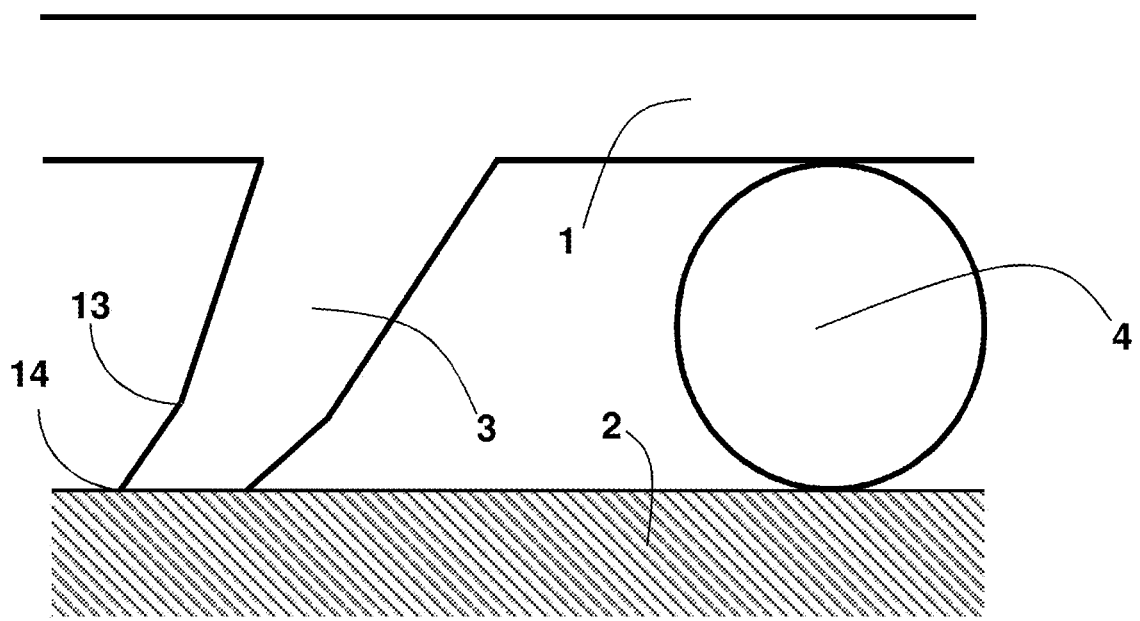
FIG. 2 shows an enlarged cross-sectional view of part of a kinked flange of a syringe of the invention.

An angled flexible flange 3 within a syringe of the invention is shown in FIG. 2 having a kinked surface 13 oriented toward the forward end of the barrel (not shown). The flange 3 is provided as a molded extension of the syringe barrel wall 1, and it extend inward to contact the plunger 2. The flange 3 has a kinked surface 13 oriented forward, the kink comprising an angle in the surface of the flange 3. The flange 3 extends to an annular edge 14 having a circumference greater than the outer circumference of the shaft.

The invention claimed is:

1. A syringe for dispensing medical foam comprising:
   a substantially cylindrical barrel comprising a nozzle at its forward end;
   a plunger comprising a substantially cylindrical shaft disposed within the barrel; and
   a flexible, annular flange provided on the inner surface of the barrel, the flange including a base affixed to the inner surface of the barrel and an inwardly extending portion extending from the base in an inward direction away from the inner surface to an end opposite the base, the end opposite the base and the inwardly extending portion being free of direct attachment to the inner surface of the barrel and an entirety of the inwardly extending portion being angled toward the nozzle to contact the shaft, wherein at least a portion of the flange is movable toward the shaft in response to pressure of fluid in the barrel to thereby form a seal between the barrel and the plunger.

2. The syringe according to claim 1 wherein the flange is mechanically fixed to the inner surface of the barrel.

3. The syringe according to claim 1 wherein the flange is flexible over its entire surface area.

4. The syringe according to claim 1 wherein the flange is tapered from a thicker base to have reduced thickness at a point at which it contacts the shaft.

5. The syringe according to claim 1 wherein the flange extends generally forwards and generally inwards and contacts the shaft at an angle which is less than 90°.

6. The syringe according to claim 1 wherein the flange has a generally frustoconical shape.

7. The syringe according to claim 1 wherein the flange extends to an annular edge having a circumference that is equal to or less than the outer circumference of the shaft.

8. The syringe according to claim 1 wherein the flange extends to an annular edge having a circumference that is greater than the outer circumference of the shaft such that foam within the barrel deforms the flange to contact the shaft, and such that the flange forms a seal between the barrel and the plunger.

9. A syringe for dispensing medical foam comprising:

a substantially cylindrical barrel comprising a nozzle at its forward end;

a plunger comprising a substantially cylindrical shaft disposed within the barrel; and a flexible, annular flange provided on the inner surface of the barrel, the flange including a thicker base portion affixed on the inner surface of the barrel, and a thinner inwardly extending portion extending from the base in an inward direction away from the inner surface to an end opposite the base, the end opposite the base and the thinner inwardly extending portion being free of attachment to the barrel and an entirety of the thinner inwardly extending portion being angled toward the nozzle to contact the shaft, wherein at least a portion of the flange is movable toward the shaft in response to pressure of fluid in the barrel to thereby form a seal between the barrel and the plunger;

wherein the flexible annular flange is tapered from the thicker base to have reduced thickness at a point at which it contacts the shaft.

\* \* \* \* \*